United States Patent
Park et al.

(10) Patent No.: US 10,335,088 B2
(45) Date of Patent: Jul. 2, 2019

(54) APPARATUS AND METHOD FOR DETECTING BIOMETRIC INFORMATION

(71) Applicants: SAMSUNG ELECTRONICS CO., LTD., Suwon-si (KR); SEOUL NATIONAL UNIVERSITY R&DB FOUNDATION, Seoul (KR)

(72) Inventors: Sangyun Park, Hwaseong-si (KR); Yongjoo Kwon, Yongin-si (KR); Younho Kim, Hwaseong-si (KR); Heechan Kim, Seoul (KR); Jonghyun Park, Seoul (KR); Byeongwook Yoo, Bucheon-si (KR)

(73) Assignees: SAMSUNG ELECTRONICS CO., LTD., Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 684 days.

(21) Appl. No.: 15/057,581

(22) Filed: Mar. 1, 2016

(65) Prior Publication Data
US 2016/0278704 A1  Sep. 29, 2016

(30) Foreign Application Priority Data
Mar. 23, 2015 (KR) .................. 10-2015-0040208

(51) Int. Cl.
*A61B 5/00* (2006.01)
*A61B 5/02* (2006.01)
(Continued)

(52) U.S. Cl.
CPC .............. *A61B 5/6843* (2013.01); *A61B 5/02* (2013.01); *A61B 5/021* (2013.01);
(Continued)

(58) Field of Classification Search
CPC ....... A61B 5/6843; A61B 5/02; A61B 5/7225; A61B 5/681; A61B 5/02007; A61B 5/021;
(Continued)

(56) References Cited

U.S. PATENT DOCUMENTS

| | | | | |
|---|---|---|---|---|
| 5,385,144 A | * | 1/1995 | Yamanishi | A61B 5/02433 600/330 |
| 5,836,990 A | | 11/1998 | Li | |

(Continued)

FOREIGN PATENT DOCUMENTS

| | | |
|---|---|---|
| JP | 3-13154 A | 1/1991 |
| JP | 2003-47601 A | 2/2003 |

(Continued)

OTHER PUBLICATIONS

Geun, et al., "Measurement Site and Applied Pressure Consideration in Wrist Photoplethysmography", Jan. 2008, The 23rd International Technical Conference on Circuits/Systems, Computers and Communications, 5 pages total.

*Primary Examiner* — Eric F Winakur
*Assistant Examiner* — Abid A Mustansir
(74) *Attorney, Agent, or Firm* — Sughrue Mion, PLLC (57) ABSTRACT

A biometric information detecting apparatus includes a bio-signal measurer including a light-emitting unit and a light-receiving unit, the light-emitting unit configured to emit an optical signal and the light-receiving unit configured to detect the optical signal that is modulated by a target object; a low-frequency signal obtainer configured to obtain a low-frequency signal from the bio-signal measured by the bio-signal measurer; and a signal processor configured to analyze biometric information from the bio-signal in response to determining that the low-frequency signal obtained from the bio-signal is within a reference range.

20 Claims, 8 Drawing Sheets

(51) Int. Cl.
    *A61B 5/021*     (2006.01)
    *A61B 5/026*     (2006.01)
    *A61B 5/1455*     (2006.01)

(52) U.S. Cl.
    CPC ......... *A61B 5/02007* (2013.01); *A61B 5/0261* (2013.01); *A61B 5/14552* (2013.01); *A61B 5/681* (2013.01); *A61B 5/7225* (2013.01); *A61B 5/742* (2013.01)

(58) Field of Classification Search
    CPC ... A61B 5/742; A61B 5/0261; A61B 5/14552; A61B 5/02255
    See application file for complete search history.

(56) References Cited

U.S. PATENT DOCUMENTS

| | | |
|---|---|---|
| 7,103,407 B2 | 9/2006 | Hjelt et al. |
| 7,425,199 B2 | 9/2008 | Hoctor et al. |
| 7,674,230 B2 | 3/2010 | Reisfeld |
| 8,355,767 B2 | 1/2013 | Hunter et al. |
| 9,476,961 B2 | 10/2016 | Kang et al. |
| 2011/0282219 A1 | 11/2011 | Parzy et al. |
| 2012/0323095 A1* | 12/2012 | Baker, Jr. ........... A61B 5/14551 600/324 |
| 2013/0012792 A1* | 1/2013 | Addison ............ A61B 5/14551 600/324 |
| 2016/0015282 A1 | 1/2016 | Kim et al. |
| 2016/0045143 A1 | 2/2016 | Lee et al. |

FOREIGN PATENT DOCUMENTS

| | | |
|---|---|---|
| JP | 2011-200608 A | 10/2011 |
| KR | 10-2008-0046969 A | 5/2008 |

* cited by examiner

SECTION 1

FIG. 8B

SECTION 2

FIG. 9

APPARATUS AND METHOD FOR DETECTING BIOMETRIC INFORMATION

CROSS-REFERENCE TO RELATED APPLICATION

This application claims priority from Korean Patent Application No. 10-2015-0040208, filed on Mar. 23, 2015, in the Korean Intellectual Property Office, the disclosure of which is incorporated herein by reference in its entirety.

BACKGROUND

1. Field

Apparatuses and methods consistent with exemplary embodiments relate to detecting biometric information.

2. Description of the Related Art

Along with an increased interest in health and well-being, various types of biometric information measuring devices are being developed. In particular, as various types of wearable devices that may be worn become popular, exclusive devices for health care are being developed.

Generally, methods of detecting biometric information, such as pulse waves, may include invasive methods and non-invasive methods. Recently, non-invasive methods of easily detecting pulse waves without inflicting pain on a target object are widely used.

For accurate pulse wave analysis (PWA), it is desirable to obtain information based on optical signals or pressure signals at a fixed location on a body surface. Biometric information regarding a target object may be obtained based on such information, and various methods may be used to reduce measurement errors.

SUMMARY

One or more exemplary embodiments provide methods and apparatuses for accurately detecting biometric information.

Additional aspects will be set forth in part in the description which follows and, in part, will be apparent from the description, or may be learned by practice of the presented exemplary embodiments.

According to an aspect of an exemplary embodiment, provided is a biometric information detecting apparatus including: a bio-signal measurer including a light-emitting unit and a light-receiving unit, the light-emitting unit configured to emit an optical signal and the light-receiving unit configured to detect the optical signal that is modulated by a target object; a low-frequency signal obtainer configured to obtain a low-frequency signal from the bio-signal measured by the bio-signal measurer; and a signal processor configured to analyze biometric information from the bio-signal in response to determining that the low-frequency signal obtained from the bio-signal is within a reference range.

The bio-signal may include a photoplethysmogram (PPG) signal.

The biometric information detecting apparatus may further include a display configured to display an indication indicating whether a contact pressure between the biometric information detecting apparatus and a skin of the target object has an acceptable level.

The contact pressure between the biometric information detecting apparatus and the skin of the target object may be adjustable by adjusting a state in which the biometric information detecting apparatus is worn on the target object.

The display may be configured to display an indication that the contact pressure has the acceptable level when the low-frequency signal is within the reference range.

The biometric information detecting apparatus may further include a pulse signal detection controller configured to pass the bio-signal of a particular band, and provide the bio-signal of the particular band to the signal processor, wherein the signal processor is further configured to analyze the biometric information by using the bio-signal of the particular band.

The pulse signal detection controller may include a band pass filter configured to pass only a signal of the particular band.

The low-frequency signal obtainer may include a low-frequency band pass filter configured to pass only a signal of a low-frequency band.

The low-frequency band pass filter may be configured to pass only a signal of a frequency band from direct current (DC) to about 10 Hz.

The biometric information detecting apparatus may include a wearable device.

The biometric information may include at least one from among systolic blood pressure, diastolic blood pressure, oxygen saturation of blood, blood vessel elasticity, speed of blood flow, and arterial stiffness.

According to an aspect of another exemplary embodiment, provided is a method of detecting biometric information in a biometric information detecting apparatus, the method including: measuring a bio-signal by detecting an optical signal that is modulated by a target object; obtaining a low-frequency signal from the bio-signal; and in response to determining that the low-frequency signal obtained from the bio-signal is within a reference range, obtaining biometric information by analyzing a waveform of the bio-signal.

The method may further include in response to determining that the low-frequency signal is not within the reference range, again measuring the bio-signal after a state in which the biometric information detecting apparatus is worn on the target object is adjusted.

The method may further include displaying an indication indicating whether a contact pressure between the biometric information detecting apparatus and a skin of the target object has an acceptable level.

The display may be configured to display an indication that the contact pressure has the acceptable level when the low-frequency signal is within the reference range.

The bio-signal may include a PPG signal.

The method may further include filtering, by using a band pass filter, the bio-signal so that only the bio-signal of a particular band is passed, wherein the biometric information is obtained by analyzing a waveform of the filtered bio-signal.

The low-frequency signal may be obtained by passing only the bio-signal of a low frequency band by using a low-frequency band pass filter.

The low-frequency band pass filter may be configured to pass only the bio-signal of a frequency band from DC to about 10 Hz.

According to an aspect of still another exemplary embodiment, provided is a biometric information detecting apparatus including: a biometric sensor configured to sense a biometric signal of a user measured through contact with a skin of the user; a filter configured to filter a low-frequency signal from the biometric signal sensed by the biometric sensor; and a signal processor configured to determine that the biometric signal sensed by the biometric sensor is reliably sensed by the biometric sensor based on the low-frequency signal filtered by the filter, and analyze biometric information of the biometric signal in response to determining that the biometric signal is reliably sensed by the biometric sensor.

BRIEF DESCRIPTION OF THE DRAWINGS

The above and/or other aspects will become more apparent by describing certain exemplary embodiments with reference to the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects thereof. In the drawings, lengths and sizes of layers and regions may be exaggerated for clarity. As used herein, the term "and/or" includes any and all combinations of one or more of the associated listed items. Expressions such as "at least one of," when preceding a list of elements, modify the entire list of elements and do not modify the individual elements of the list.

It will be understood that, although the terms first, second, third, etc., may be used herein to describe various elements, components, regions, layers and/or sections, these elements, components, regions, layers and/or sections should not be limited by these terms.

The terminology used herein is for the purpose of describing particular exemplary embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In addition, the terms "-er", "-or", and "module" described in the specification mean units for processing at least one function and operation and can be implemented by hardware components or software components and combinations thereof.

In a method of estimating blood pressure of a user by using a photoplethysmogram (PPG), a shape and a size of a pulse component of the PPG are important variables. However, the shape and size of the pulse component of the PPG may be changed by contact pressure between a measuring device and skin. Therefore, contact pressure between a measuring device and the skin is an important factor in the case of estimating blood pressure of a user by using the PPG.

A biometric information detecting apparatus according to an exemplary embodiment is configured to increase accuracy of detecting biometric information in consideration of pressure applied by a measurer to the skin of a user. For example, when a biometric information detecting apparatus according to an exemplary embodiment is embodied as a wearable device, such as a wrist type wearable device, to measure blood pressure of a user by using PPG, the blood pressure of the user may be accurately measured in consideration of pressure applied by a measurer to the skin of the user.

Figure 1:
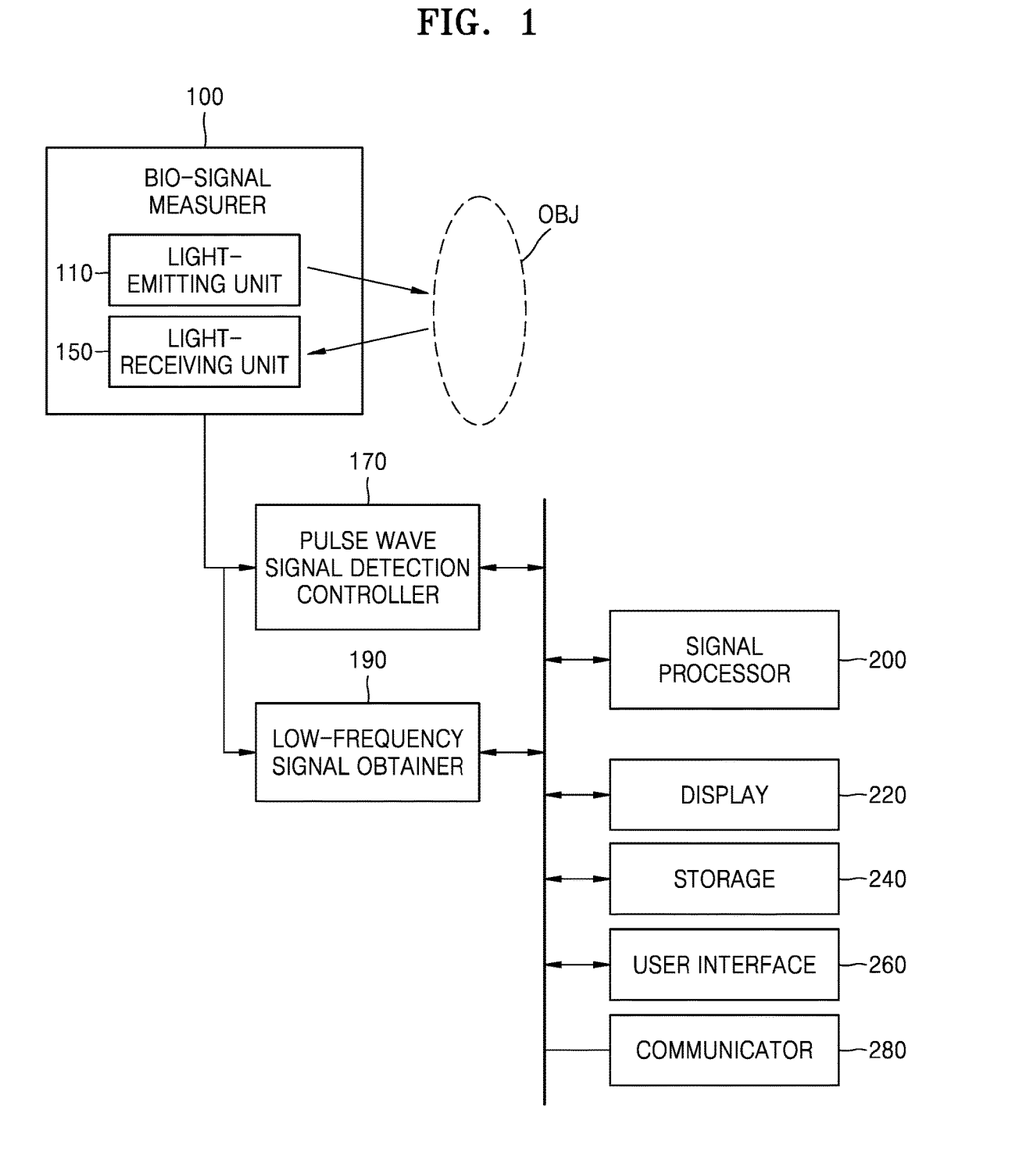
FIG. 1 is a schematic block diagram showing a configuration of a biometric information detecting apparatus according to an exemplary embodiment.

FIG. 1 is a schematic block diagram showing a configuration of a biometric information detecting apparatus according to an exemplary embodiment. The biometric information detecting apparatus according to an exemplary embodiment may measure various biometric information that may be obtained by using PPG. For example, systolic blood pressure or diastolic blood pressure, oxygen saturation of blood, blood vessel elasticity, blood flow speed, and arterial stiffness may be estimated. Hereinafter, descriptions will be given regarding a case in which bio-signals are detected in the form of PPGs. However, an exemplary embodiment is not limited thereto. The biometric information detecting apparatus according to an exemplary embodiment may be applied to detection of various biometric information by applying pressure to the skin of a user.

Referring to FIG. 1, the biometric information detecting apparatus is an apparatus for detecting biometric information regarding a target object OBJ and includes a bio-signal measurer 100, a low-frequency signal obtainer 190, and a signal processor 200. The biometric information detecting apparatus may further include a display 220. The biometric information detecting apparatus may further include a pulse signal detection controller 170 such that bio-signals input to the signal processor 200 include more optimal pulse components, for example. Furthermore, the biometric information detecting apparatus may further include at least one of a storage 240, a user interface 260, and a communicator 280.

The bio-signal measurer 100 includes a light-emitting unit 110 and a light-receiving unit 150. The light-emitting unit 110 generates an optical signal, and the light-receiving unit 150 detects the optical signal that is modulated by the target object OBJ, thereby measuring a bio-signal.

In the bio-signal measurer 100, the light-emitting unit 110 may include at least one light emitting diode (LED) or at least one laser diode (LD). The light-emitting unit 110 may also include a combination of at least one LED and at least one LD. The light-receiving unit 150 includes at least one light receiving element. Examples of light receiving elements may include a photo diode, a photo transistor (PTr), or an image sensor, such as a charge-coupled device (CCD) or a complementary metal-oxide semiconductor (CMOS). The light receiving element may detect optical signals that are scattered and/or reflected by the target object OBJ.

The bio-signal measurer 100 may be arranged to irradiate a light beam generated by the light-emitting unit 110 to the target object OBJ and to detect the light beam that is modulated by the target object OBJ, e.g., the light beam that is scattered and/or reflected by the target object OBJ, via the light-receiving unit 150. A bio-signal detected by the light-receiving unit 150 of the bio-signal measurer 100, e.g., a PPG signal, may be input to the signal processor 200 and the low-frequency signal obtainer 190. If the pulse signal detection controller 170 is further arranged between the bio-signal measurer 100 and the signal processor 200, a bio-signal, e.g., a PPG signal, may be input to the signal processor 200 in a state including a pulse component via the pulse signal detection controller 170.

Here, the PPG signal is obtained by detecting fluctuations of an optical signal corresponding to a change of a volume of a blood vessel (e.g., a radial artery) of the target object OBJ and may be obtained based on a correlation between a change in an optical signal and a change in a volume of a blood vessel.

The target object OBJ is a target object for detecting biometric information, may be a biological portion that may contact or be adjacent to the bio-signal measurer 100 of the biometric information detecting apparatus 10, and may be a body part at which pulse waves may be easily measured via photoplethysmography (PPG). For example, the target object OBJ may be a portion of a wrist near a radial artery. When pulse waves are measured at a surface of a wrist at a position along which a radial artery extends, effects from external factors causing measurement errors, e.g., thickness of tissue inside the wrist may be relatively small. Furthermore, a radial artery is known as a blood vessel that may be used for measuring blood pressure at a relatively high accuracy compared to other blood vessels in a wrist. However, the target object OBJ is not limited to a radial artery and may be other peripheral body parts with a high blood vessel density, e.g., a finger, a toe, an earlobe, etc.

The pulse signal detection controller 170 is a unit for filtering a bio-signal measured by the bio-signal measurer 100 so that only a particular band of the bio-signal, e.g., a pulse component, is filtered and input to the signal processor 200.

Figure 2:
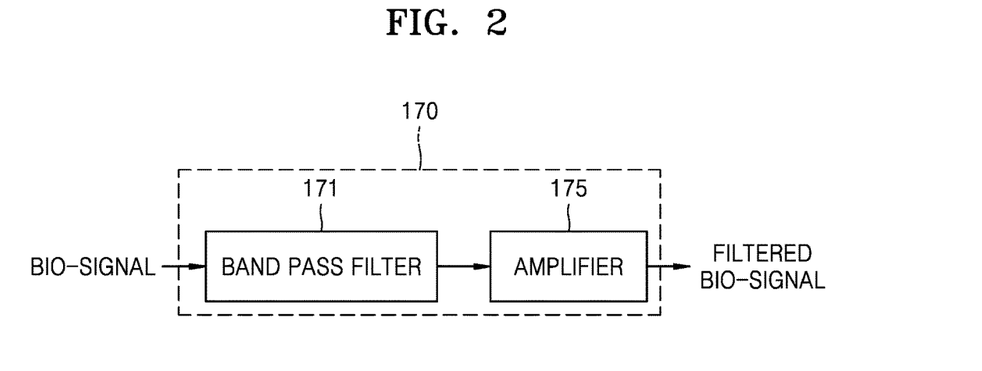
FIG. 2 is a schematic block diagram showing an exemplary embodiment of a pulse signal detection controller of FIG. 1.

Referring to FIG. 2, the pulse signal detection controller 170 may include a band pass filter 171, which passes only a particular band of a bio-signal, e.g., a band of a pulse signal. Furthermore, the pulse signal detection controller 170 may further include an amplifier 175 for amplifying a bio-signal that has passed through the band pass filter 171. By using the pulse signal detection controller 170, a filtered bio-signal including a pulse signal component may be obtained.

Here, as described below, a PPG signal includes a low frequency component that varies according to a degree of contact between a biometric information detecting apparatus and the skin of the target object OBJ, that is, contact pressure, and the pulse signal detection controller 170 may remove a low frequency component included in a bio-signal. Furthermore, the pulse signal detection controller 170 may remove a high frequency component other than a pulse component. FIG. 1 shows a case in which the biometric information detecting apparatus according to an exemplary embodiment includes the pulse signal detection controller 170 between the bio-signal measurer 100 and the signal processor 200. However, it is merely an example, and a biometric information detecting apparatus according to an exemplary embodiment may have a structure without the pulse signal detection controller 170. In other words, a biometric information detecting apparatus according to an exemplary embodiment may be configured such that a bio-signal detected by the bio-signal measurer 100 is directly input to the signal processor 200. In a structure where a bio-signal is directly input to the signal processor 200, the signal processor 200 may be arranged to perform an operation to remove components of an input bio-signal.

The low-frequency signal obtainer 190 may obtain a low-frequency signal from a bio-signal measured by the bio-signal measurer 100.

Figure 3:
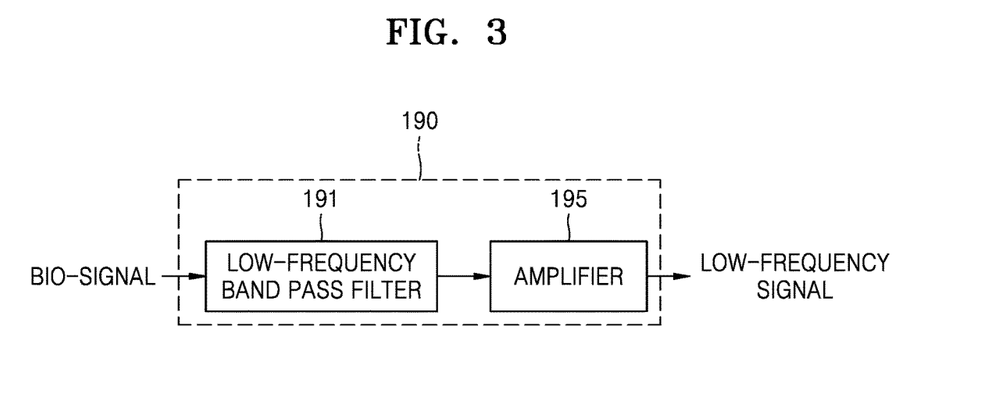
FIG. 3 is a schematic block diagram showing an exemplary embodiment of a low-frequency signal obtainer of FIG. 1.

Referring to FIG. 3, the low-frequency signal obtainer 190 may include a low-frequency band pass filter 191 for passing only low-frequency signals therethrough. Furthermore, the low-frequency signal obtainer 190 may further include an amplifier 195, which amplifies a low-frequency signal that has passed through the low-frequency band pass filter 191, and the amount of amplification may be by from several times to hundreds of times, for example. The low-frequency band pass filter 191 may be arranged to pass a signal of a low frequency band from, for example, 0 Hz (i.e., direct current (DC)) to about 10 Hz therethrough. For example, the low-frequency band pass filter 191 is arranged to pass a signal of a low frequency band from DC (i.e., 0 Hz) to about 1 Hz therethrough (e.g., from DC to about 0.1 Hz), for example, and the amplifier 195 may be arranged to amplify, by about five times, a low-frequency signal that has passed through the low-frequency band pass filter 191. In another example, the low-frequency band pass filter 191 may be arranged to pass a signal of a low frequency band from about 0.3 Hz to about 10 Hz therethrough, and the amplifier 195 may be arranged to amplify, by about 200 times, a low-frequency signal passed through the low-frequency band pass filter 191.

A low-frequency signal obtained by the low-frequency signal obtainer 190 may be used to estimate a degree of contact and contact pressure between a biometric information detecting apparatus and the skin of the target object OBJ. As described below, a PPG signal includes a low frequency component that varies according to a degree of contact between a biometric information detecting apparatus and the skin of the target object OBJ, that is, contact pressure. Therefore, only a low frequency component of a PPG signal is extracted by using the low-frequency signal obtainer 190 and a degree of contact and contact pressure between a biometric information detecting apparatus and the skin of the target object OBJ may be estimated by using the low frequency component of a PPG signal that is extracted.

When a low-frequency signal obtained by the low-frequency signal obtainer 190 is within a reference range, that is, a degree of contact between a biometric information detecting apparatus and the skin of the target object OBJ is within an appropriate (or acceptable) pressure range, the signal processor 200 analyzes a waveform of an input bio-signal and thereby analyzes biometric information. As described below, the reference range may correspond to a range of low-frequency signals, that is, DC values obtained under a contact pressure at which a bio-signal, e.g., a PPG signal, exhibits valid signal properties.

A low-frequency signal obtained by the low-frequency signal obtainer 190 and a bio-signal from the bio-signal measurer 100 may be input to the signal processor 200. When the pulse signal detection controller 170 is further included, a bio-signal input to the signal processor 200 may be a signal via the pulse signal detection controller 170.

The signal processor 200 may analyze a waveform of a bio-signal and analyze biometric information by applying a designated algorithm for calculating biometric information. For example, the signal processor 200 may estimate biometric information including systolic blood pressure and/or diastolic blood pressure of blood vessel, oxygen saturation of blood, blood vessel elasticity, blood flow speed, and an artery stiffness by analyzing a waveform of a bio-signal and applying an algorithm for calculating biometric information.

Here, the signal processor 200 analyzes a waveform of a bio-signal and calculates biometric information only when a low-frequency signal obtained by the low-frequency signal obtainer 190 is within a reference range, and thus more accurate biometric information may be calculated.

The display 220 may display whether a user is properly contacting a biometric information detecting apparatus on the skin in real time. The display 220 is arranged to display whether contact pressure between a biometric information detecting apparatus and the skin of the target object OBJ is appropriate (e.g., the contact pressure has an acceptable level). The display 220 may be arranged to display that a contact pressure is appropriate when a low-frequency signal obtained by the low-frequency signal obtainer 190 is within the reference range. A user may adjust a state in which the biometric information detecting apparatus is worn while checking a state displayed by the display 220, thereby adjusting contact pressure between a biometric information detecting apparatus and the skin of the target object OBJ to an appropriate contact pressure.

When the display 220 displays that contact pressure is appropriate, a user may stop adjusting a wearing state of the biometric information detecting apparatus and perform a biometric information detecting process.

Programs for processing and controlling the signal processor 200 and input/output data may be stored in the storage 240. For example, a reference range, which is a reference for determining whether contact pressure between a biometric information detecting apparatus and the skin of the target object OBJ is appropriate by comparing the reference with a low-frequency signal obtained by the low-frequency signal obtainer 190, may be stored in the storage 240. Furthermore, programs for the bio-signal waveform analysis and biometric information analysis performed by the signal processor 200 may be stored in the storage 240 as codes. Furthermore, results measured by the bio-signal measurer 100 that are needed by the signal processor 200 may be stored in the storage 240.

The storage 240 may include at least one of storage media including a flash memory type storage medium, a hard disk type storage medium, a multimedia card micro type storage medium, a card type memory (e.g., a secure digital (SD) memory or an extreme digital (XD) memory), a random access memory (RAM), a static RAM (SRAM), a read-only memory (ROM), an electrically erasable-programmable ROM (EEPROM), a programmable ROM (PROM), a magnetic memory, a magnetic disk, and an optical disc.

The user interface 260 is an interface between a user and/or other external devices and the biometric information detecting apparatus and may include an input unit and an output unit. Here, a user may not only be an object for measuring biometric information, that is, the target object OBJ, but also be a person capable of using the biometric information detecting apparatus, such as a medical expert. Information for operating the biometric information measuring apparatus may be input via the user interface 260 and a result of analysis may be output via the user interface 260. The user interface 260 may include a button, a connector, a keypad, and a display and may further include an acoustic output unit or a vibration motor, for example. For example, when the display 220 displays that contact pressure between a biometric information detecting apparatus and the skin of the target object OBJ is appropriate, by pressing a button or a keypad, the user interface 260 may be operated to perform a process of detecting of the biometric information by the biometric information measuring apparatus. Also, when the display 220 is arranged to receive an input of information by a touch or has a touch screen, the user interface 260 may be operated to perform a process of detecting of the biometric information by the biometric information measuring apparatus through a touch on a touch region of the display.

The biometric information detecting apparatus may further include a communicator 280 for transmitting a result of analysis to an external device. The external device may be a medical device using analyzed biometric information, a printer for printing out a result of analysis, or a display apparatus for displaying a result of analysis. Furthermore, the external device may be a smart phone, a cellular phone, a personal digital assistant (PDA), a laptop personal computer (PC), a desktop PC, or various other mobile or non-mobile computing devices. The communicator 280 may be connected to the external device via a wire or wirelessly. For example, the communicator 280 may be arranged to communicate with the external device via various communication methods, such as a Bluetooth communication, a Bluetooth Low Energy (BLE) communication, a near field communication (NFC), a wireless LAN (WLAN) communication, a Zigbee communication, an infrared data association (IrDA) communication, a wi-fi direct (WFD) communication, a ultra wideband (UWB) communication, an Ant+ communication, or a Wi-Fi communication.

The biometric information detecting apparatus may also be realized in the form of a wearable device that may be worn by the target object OBJ. For example, the biometric information detecting apparatus may be realized in the form of a wrist watch, a bracelet, or a wristband. Furthermore, the biometric information detecting apparatus may also be realized in the form of a ring, an eyeglass, an earphone, or a headphone, but is not limited thereto. Alternatively, only some components of the biometric information detecting apparatus, e.g., the multi-channel bio-signal measurer 100, may be realized in the form of a wearable device that may be worn by the target object OBJ.

Figure 4:
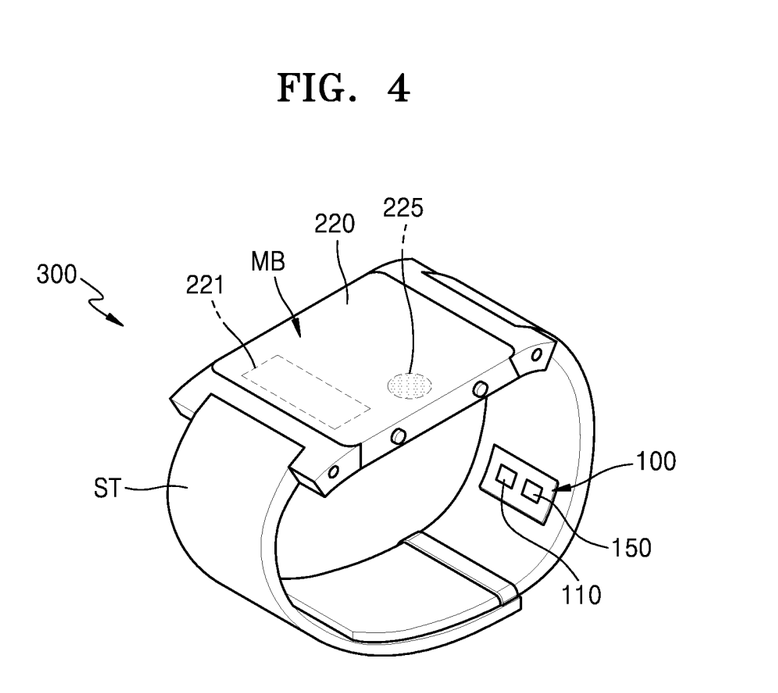
FIG. 4 is a diagram illustrating a biometric information detecting apparatus in a form of a wrist type device according to an exemplary embodiment.

FIG. 4 is a diagram illustrating a biometric information detecting apparatus 300 realized in a form of a wrist type device according to an exemplary embodiment. The biometric information detecting apparatus 300 of FIG. 4 may include the components of the biometric information detecting apparatus according to the exemplary embodiment described above with reference to FIG. 1.

Referring to FIG. 4, the biometric information detecting apparatus 300 may include a main body MB and a strap ST. The strap ST may be arranged to have a structure that is connected to two opposite ends of the main body MB to be worn on a body part (e.g., a wrist) of a user. At least some of the low-frequency signal obtainer 190, the pulse signal detection controller 170, the signal processor 200, the display 220, the storage 240, the user interface 260, and the communicator 280 of the biometric information detecting apparatus 300 may be arranged at the main body MB. The main body MB may further include a watch module, such that the biometric information detecting apparatus 300 may be used as a wristwatch.

The bio-signal measurer 100, which detects bio-signals in the proximity of the skin of the target object OBJ, may be arranged at at least one of the strap ST and the main body MB. In the biometric information detecting apparatus 300, at least the bio-signal measurer 100 may be arranged to be able to contact the skin of the target object OBJ. Contact pressure between the biometric information detecting apparatus 300 and the skin of the target object OBJ may indicate a pressure at a portion at which a bio-signal is detected by the bio-signal measurer 100.

FIG. 4 is a diagram showing a case in which the bio-signal measurer 100 is arranged on an inner surface of the strap ST. The bio-signal measurer 100 may also be arranged on a rear surface of the main body MB. In this case, contact pressure between a portion of the biometric information detecting apparatus 300 at which a bio-signal is detected by the bio-signal measurer 100 and the skin of the target object OBJ may be adjusted by adjusting the strap ST.

The display 220 may be arranged on a front surface of the main body MB. The display 220 may be operated to display whether contact pressure between the biometric information detecting apparatus 300 and the skin of the target object OBJ is appropriate. Furthermore, the display 220 may also be operated to display biometric information measured via biometric information detection, e.g., systolic blood pressure or diastolic blood pressure, oxygen saturation of blood, blood vessel elasticity, blood flow speed, and an artery stiffness.

The display 220 may include an information display region 221 for displaying whether contact pressure between the biometric information detecting apparatus 300 and the skin of the target object OBJ is appropriate or displaying biometric information. The display 220 may be arranged to further include a touch region 225 for turning an operation of the biometric information detecting apparatus 300 on and off. The display 220 may include a touch screen for displaying information and inputting information. The display 220 may include the information display region 221 only, and a button for turning an operation of the biometric information detecting apparatus 300 on and off may be separately arranged at the main body MB. Although FIG. 4 shows that the information display region 221 is located at a portion of the display 220, it is merely an example, and a size of the information display region 221 is not limited to the size as shown in FIG. 4. The entire region of the display 220 or an region of the display 220 excluding the touch region 225 may be used as the information display region 221. Descriptions will be exemplarily given below regarding a case in which the touch region 225 is arranged at the display 220.

Figure 5A:
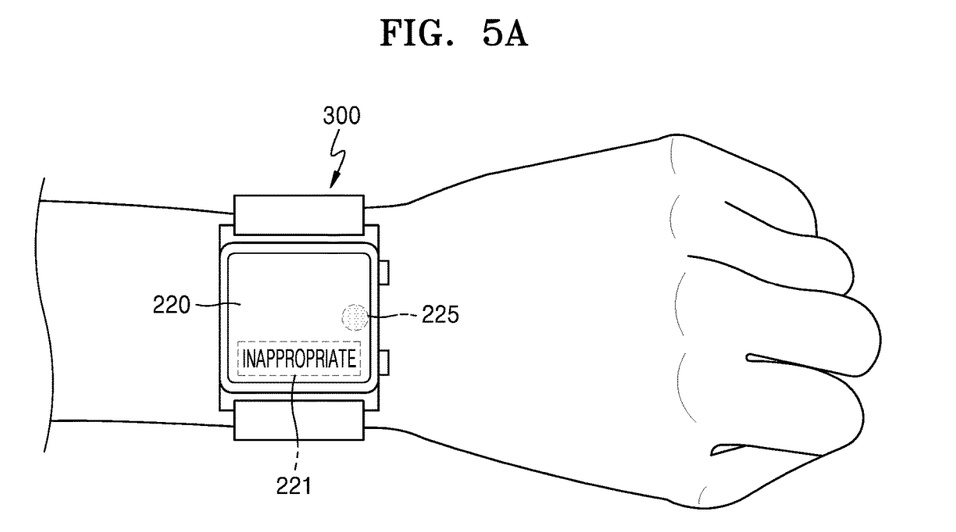
FIGS. 5A and 5B are diagrams illustrating a case in which a user wears the biometric information detecting apparatus of FIG. 4 on a wrist.
Figure 5B:
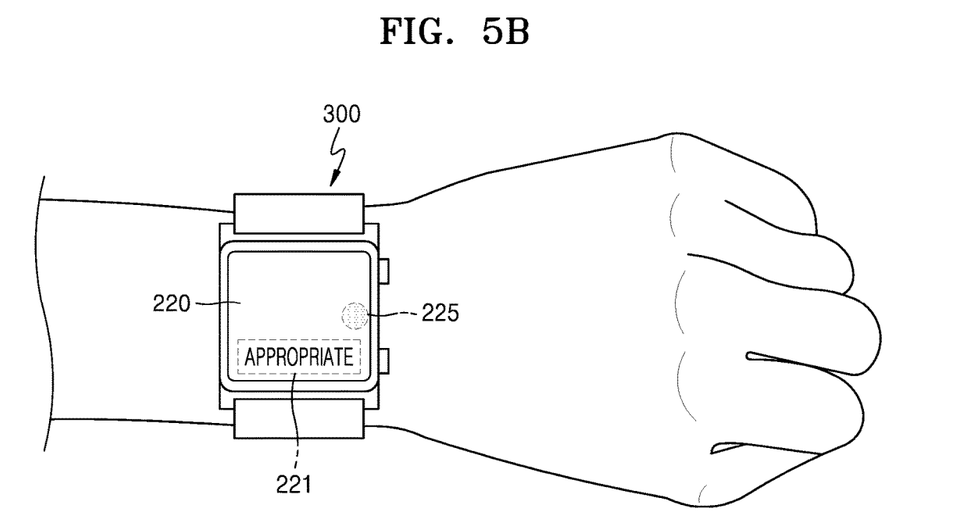

FIGS. 5A and 5B are diagrams illustrating a case in which a user wears the biometric information detecting apparatus 300 of FIG. 4 on a wrist.

When the user wears the biometric information detecting apparatus 300 on a wrist and operates the biometric information detecting apparatus 300 by touching the touch region 225, the light-emitting unit 110 of the bio-signal measurer 100 emits a light beam to the target object OBJ. A light beam modulated by the target object OBJ is detected by the light-receiving unit 150 of the bio-signal measurer 100. A bio-signal detected by the light-receiving unit 150 is input to the low-frequency signal obtainer 190 and the pulse signal detection controller 170 (or the signal processor 200). When a low-frequency signal obtained by the low-frequency signal obtainer 190 with respect to the input bio-signal is out of a reference range, the display 220 displays that the contact pressure between the biometric information detecting apparatus 300 and the skin of the target object OBJ is inappropriate as shown in FIG. 5A. When a low-frequency signal obtained by the low-frequency signal obtainer 190 with respect to the input bio-signal is within the reference range, the display 220 displays that the contact pressure between the biometric information detecting apparatus 300 and the skin of the target object OBJ is appropriate as shown in FIG. 5B.

When the display 220 displays that the contact pressure between the biometric information detecting apparatus 300 and the skin of the target object OBJ is inappropriate as shown in FIG. 5A, the user adjusts a state in which the biometric information detecting apparatus 300 is worn by adjusting the strap ST, for example, and operates the biometric information detecting apparatus 300 by touching the touch region 225 again. Here, the adjustment of the state in which the biometric information detecting apparatus 300 is worn and operation of the biometric information detecting apparatus 300 may be repeated until the display 220 displays that the contact pressure between the biometric information detecting apparatus 300 and the skin of the target object OBJ is appropriate.

When the display 220 displays that the contact pressure between the biometric information detecting apparatus 300 and the skin of the target object OBJ is appropriate as shown in FIG. 5B, the user may touch the touch region 225 again to continuously detect biometric information.

Figure 6A:
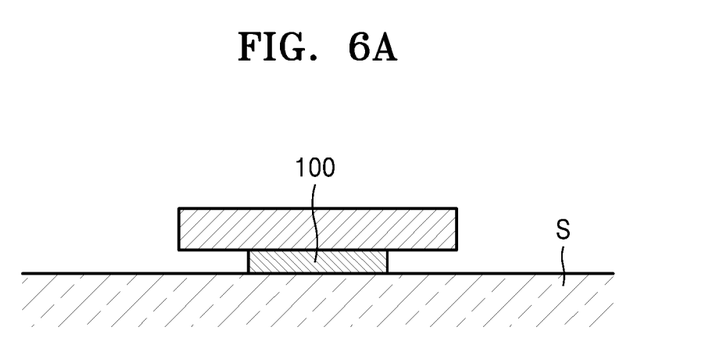
FIGS. 6A and 6B are diagrams showing an example of adjusting a wearing state of the biometric information detecting apparatus.
Figure 6B:
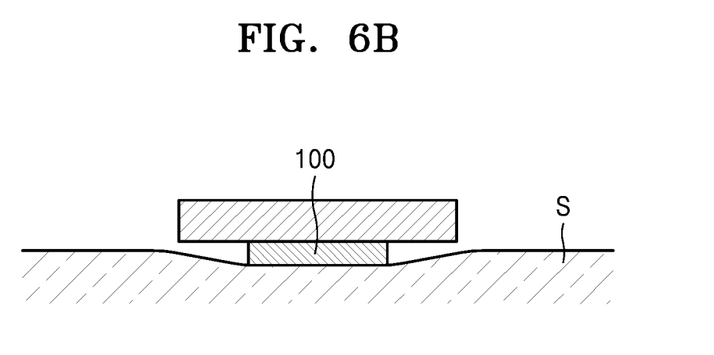

FIGS. 6A and 6B are diagrams showing an example of adjusting while a wearing state of the biometric information detecting apparatus while a portion (e.g., the bio-signal measurer 100) of a biometric information detecting apparatus at which a bio-signal is detected by the bio-signal measuring unit 100 contacts the skin S. FIG. 6A shows a state in which a portion (e.g., the bio-signal measurer 100) of the biometric information detecting apparatus at which a bio-signal is detected lightly contacts the skin S, whereas FIG. 6B shows a state in which a portion (e.g., the bio-signal measurer 100) of the biometric information detecting apparatus at which a bio-signal is detected presses the skin S. As shown in FIGS. 6A and 6B, when the state in which a biometric information detecting apparatus is worn is adjusted and contact pressure applied to the skin is changed, a bio-signal measured by the bio-signal measurer 100 is changed.

Figure 7:
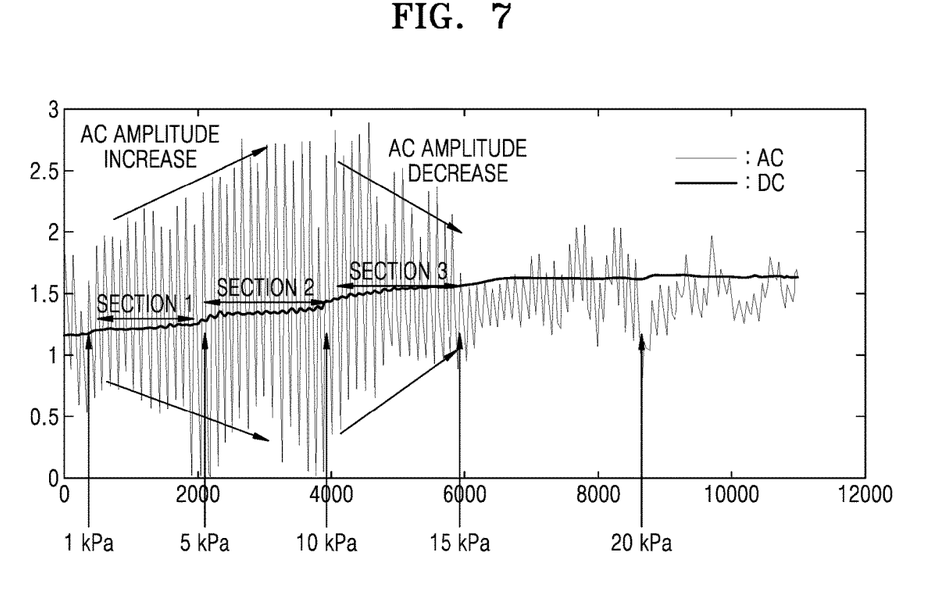
FIG. 7 is a diagram illustrating an exemplary of changes in a low frequency component of a photoplethysmography (PPG) signal when contact pressure between a biometric information detecting apparatus and a skin of a user increases.

FIG. 7 is a diagram exemplarily illustrating changes in low frequency component of a PPG signal and the PPG signal when contact pressure between a biometric information detecting apparatus and the skin of a user increases.

Referring to FIG. 7, as contact pressure increases, a low frequency component of a PPG signal increases. Furthermore, there are sections in which an alternating current (AC) component of the PPG signal increases or decreases based on contact pressures and the PPG signal does not exhibit valid signal properties at and above a designated pressure. As contact pressure increases, an AC amplitude of the PPG signal increases in the section 1 and section 2. The AC amplitude of the PPG signal decreases in the section 3, and the PPG signal does not exhibit valid signal properties under a control pressure greater than that of the section 3. Here, for example, the section 1 corresponds to a pressure range from about 1 kPa to about 5 kPa, the section 2 corresponds to a pressure range from about 5 kPa to about 10 kPa, and the section 3 corresponds to a pressure range from about 10 kPa to about 15 kPa.

Measurement of biometric information, e.g., blood pressure, by using a biometric information detecting apparatus according to an exemplary embodiment may be performed within the sections 1 through 3 in which bio-signals exhibit valid signal properties. In the section 1, a low frequency component (that is, a DC component) of a PPG signal is about 1.18 V, whereas an AC amplitude is from about 1V to about 1.5 V (e.g., about 1.3 V). In the section 2, a low frequency component (that is, a DC component) of a PPG signal is about 1.35 V, whereas an AC amplitude is about 2.2 V. In the section 3, a low frequency component (that is, a DC component) of a PPG signal is about 1.45 V, whereas an AC amplitude decreases from about 2.2 V to about 1V.

When a PPG signal exhibits the signal properties shown in FIG. 7, a reference range of low-frequency signals corresponding to an appropriate contact pressure between a biometric information detecting apparatus and the skin of the target object OBJ is from about 1.18 V to about 1.45 V. Therefore, when a low-frequency signal level of the PPG signal, that is, a low-frequency signal obtained by the low-frequency signal obtainer 190 is out of the range from about 1.18 V to about 1.45 V, contact pressure is adjusted by adjusting a state in which a biometric information detecting apparatus is worn. When the low-frequency signal is within the range from about 1.18 V to about 1.45 V, blood pressure is estimated based on a low-frequency signal level and a peak-to-peak value of an AC component of the PPG.

Figure 8A:
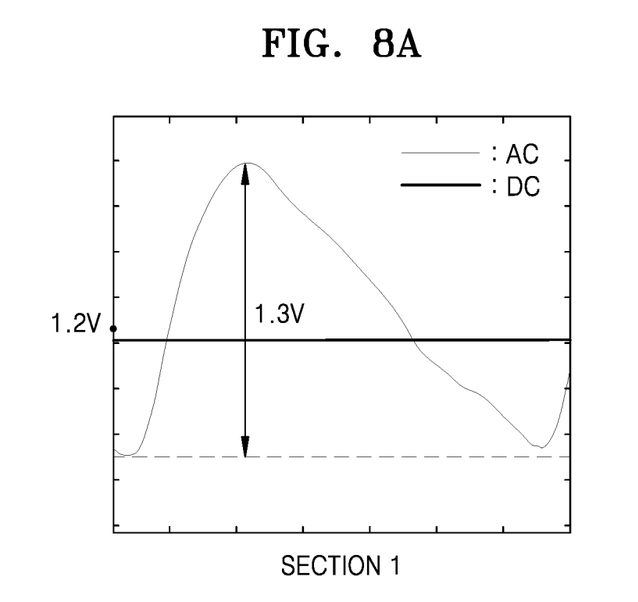
FIGS. 8A and 8B are diagrams showing examples of direct current (DC) components of a PPG signal and sizes of alternating current (AC) amplitudes in a section 1 and a section 2 of FIG. 7.
Figure 8B:
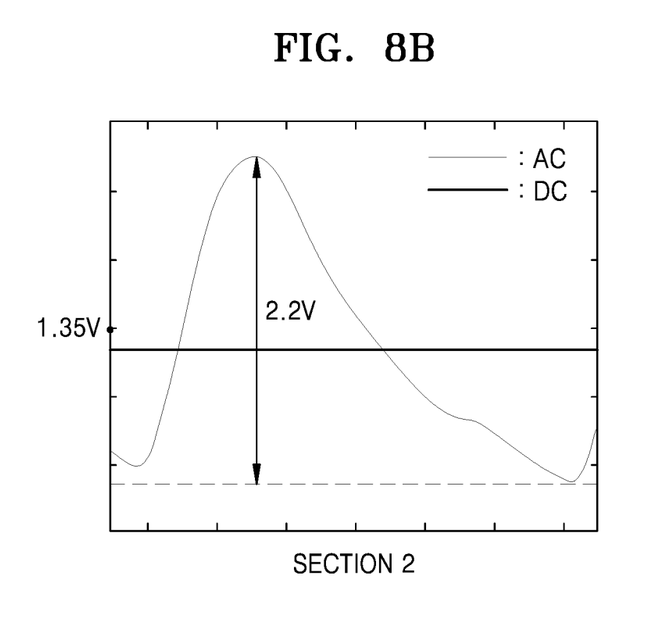

FIGS. 8A and 8B are diagrams showing examples of DC components of the PPG signal and sizes of AC amplitudes in the section 1 and the section 2 of FIG. 7.

In FIGS. 7, 8A, and 8B, the contact pressures, and the low frequency components and the AC amplitudes of the PPG signals are merely examples, where the values may vary based on measuring conditions, a signal amplification rate, etc.

The state in which a biometric information detecting apparatus is worn, according to an exemplary embodiment, may be adjusted to satisfy a contact pressure within a range in which detected PPG signals exhibit valid signal properties. It may be determined whether a detected PPG signal is within a range in which valid signal properties may be exhibited by determining, by the signal processor 200, whether a low-frequency signal of a detected bio-signal is within a pre-set reference range or an AC amplitude of the detected bio-signal is equal to or greater than a reference value.

Figure 9:
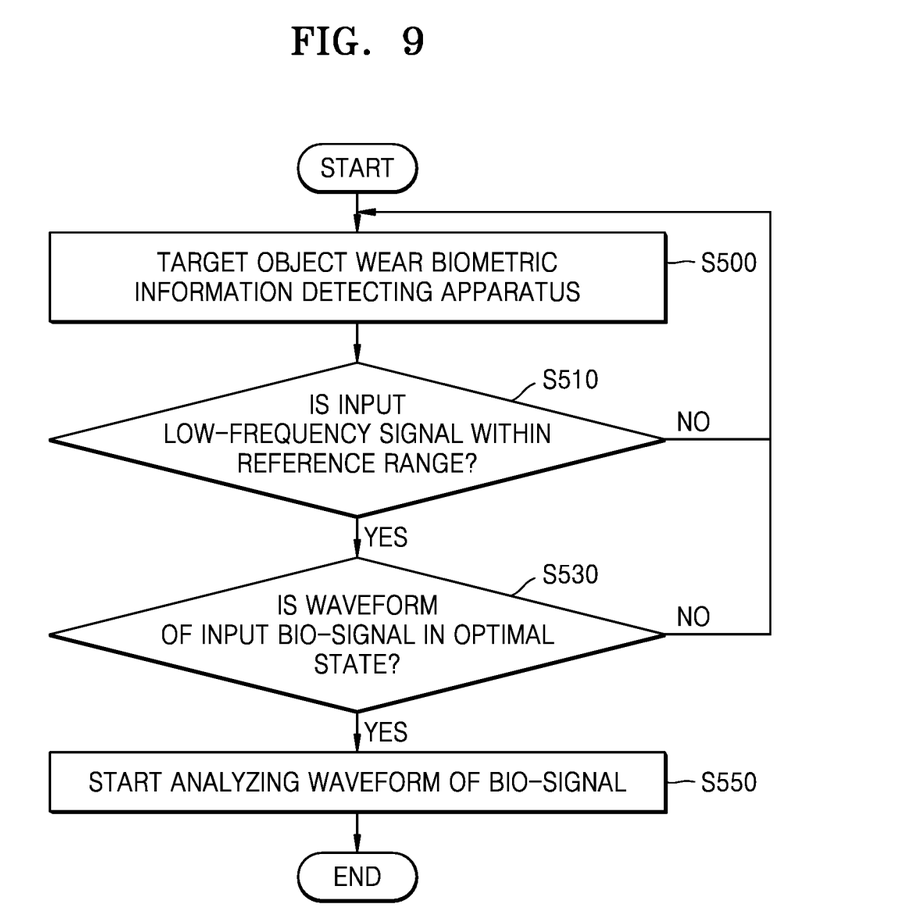
FIG. 9 is a flowchart of a method of operating a biometric information detecting apparatus according to an exemplary embodiment.

FIG. 9 is a flowchart for describing a method of operating a biometric information detecting apparatus according to an exemplary embodiment.

Referring to FIG. 9, when the biometric information detecting apparatus receives a command to measure biometric information while the biometric information detecting apparatus is being worn by the target object OBJ, the light-emitting unit 110 of the bio-signal measurer 100 emits a light beam to the target object OBJ, and the light-receiving unit 150 detects a bio-signal (e.g., a PPG signal) (operation S500).

The detected bio-signal is input to the low-frequency signal obtainer 190 and the pulse signal detection controller 170 (or the signal processor 200). The low-frequency signal obtainer 190 outputs only a low-frequency signal from the input bio-signal, e.g., a low frequency component of a PPG signal. The low-frequency signal may be obtained by passing only signals of a low frequency band through a low-frequency band pass filter. Here, the low-frequency band pass filter may be arranged to pass only signals of a low frequency band from DC to about 10 Hz therethrough. A low-frequency signal passed through the low-frequency band pass filter may be amplified by a designated amplification, where a low-frequency signal obtained by the low-frequency signal obtainer 190 is input to the signal processor 200.

Furthermore, the detected bio-signal is input to the signal processor 200 directly or via the pulse signal detection controller 170. Here, the pulse signal detection controller 170 filters bio-signals measured by the bio-signal measurer 100 to pass only signals of a particular band through a band pass filter. The filtered bio-signal may be amplified by an appropriate amplification factor by using an amplifier.

The signal processor 200 determines whether a low-frequency signal obtained by the low-frequency signal obtainer 190 is within a reference range (operation S510). When a low-frequency signal obtained by the low-frequency signal obtainer 190 is within the reference range, biometric information is extracted by analyzing waveform of an input bio-signal. When a low-frequency signal obtained by the low-frequency signal obtainer 190 is not within the reference range, a state in which the biometric information detecting apparatus is worn is adjusted, and the method returns to the operation for measuring a bio-signal. Here, the pressure applied by the biometric information detecting apparatus to the skin of the target object OBJ is adjusted by adjusting the state in which the biometric information detecting apparatus is worn.

The display 220 may display whether contact pressure between a biometric information detecting apparatus and the skin of the target object OBJ is appropriate, such that a user may visually determine whether to adjust the state in which the biometric information detecting apparatus is worn. In other words, the user may adjust the state in which the biometric information detecting apparatus is worn while checking a state displayed by the display 220, thereby adjusting contact pressure between the biometric information detecting apparatus and the skin of the target object OBJ.

When a low-frequency signal is within the reference range, the display 220 may display that contact pressure is appropriate. When a low-frequency signal is out of the reference range, the display 220 may display that contact pressure is inappropriate.

When the low-frequency signal is within a reference range, it may be determined whether a waveform of a bio-signal input to the signal processor 200 is in optimal state (operation S530) and, when the waveform of the bio-signal is optimal, analysis of the waveform of the bio-signal may be started (operation S550). The optimal state of waveform of a bio-signal may refer to a state at which contact pressure between a biometric information detecting apparatus and the skin of the target object OBJ is appropriate and the bio-signal exhibits valid signal properties. Here, the operation 530 for determining whether a waveform of a bio-signal input to the signal processor 200 is in optimal state may be omitted.

As described above, according to the one or more of the above exemplary embodiments, a biometric information detecting apparatus may estimate a contact pressure between a biometric information detecting apparatus and the skin of the target object OBJ by using a PPG signal, and thus cardiovascular characteristics, e.g., blood pressure, blood vessel elasticity, blood vessel stiffness, cardiovascular age, etc., may be analyzed by using a PPG signal under an appropriate pressure.

At least one of the components, elements or units represented by a block as illustrated in FIGS. 1 to 3 may be embodied as various numbers of hardware, software and/or firmware structures that execute respective functions described above, according to an exemplary embodiment. For example, at least one of these components, elements or units may use a direct circuit structure, such as a memory, processing, logic, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions. Also, at least one of these components, elements or units may further include a processor such as a central processing unit (CPU) that performs the respective functions, a microprocessor, or the like. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

Although a few embodiments have been shown and described, it would be appreciated by those skilled in the art that changes may be made in the exemplary embodiments without departing from the principles and spirit of the disclosure, the scope of which is defined in the claims and their equivalents.

What is claimed is:

1. A biometric information detecting apparatus comprising:
    a bio-signal measurer configured to measure a bio-signal and comprising a light emitter and a light receiver, the light emitter being configured to emit an optical signal and the light emitter being configured to detect the optical signal that is modulated by a target object;
    a low-frequency signal obtainer circuitry configured to obtain a low-frequency signal from the bio-signal measured by the bio-signal measurer; and
    a signal processor configured to analyze a waveform of the bio-signal in response to determining that the low-frequency signal obtained from the bio-signal is within a reference range,
    wherein the signal processor does not start analyzing the waveform of the bio-signal until it is determined that the low-frequency signal obtained from the bio-signal is within the reference range.

2. The biometric information detecting apparatus of claim 1, wherein the bio-signal comprises a photoplethysmogram (PPG) signal.

3. The biometric information detecting apparatus of claim 1, further comprising a display configured to display an indication indicating whether a contact pressure between the biometric information detecting apparatus and a skin of the target object has an acceptable level.

4. The biometric information detecting apparatus of claim 3, wherein the bio-signal measurer is configured to, in response to determining that the low-frequency signal is not within the reference range, again measure the bio-signal after a state in which the biometric information detecting apparatus is worn on the target object is adjusted.

5. The biometric information detecting apparatus of claim 4, wherein the display is configured to display an indication that the contact pressure has the acceptable level when the low-frequency signal is within the reference range.

6. The biometric information detecting apparatus of claim 1, further comprising:
    a pulse signal detection controller configured to pass the bio-signal of a particular band, and provide the bio-signal of the particular band to the signal processor,
    wherein the signal processor is further configured to analyze the waveform of the bio-signal by using the bio-signal of the particular band.

7. The biometric information detecting apparatus of claim 6, wherein the pulse signal detection controller comprises a band pass filter configured to pass only a signal of the particular band.

8. The biometric information detecting apparatus of claim 1, wherein the low-frequency signal obtainer circuitry comprises a low-frequency band pass filter configured to pass only a signal of a low-frequency band.

9. The biometric information detecting apparatus of claim 8, wherein the low-frequency band pass filter is configured to pass only a signal of direct current (DC) and a signal of a frequency band less than 10 Hz.

10. The biometric information detecting apparatus of claim 1, wherein the biometric information detecting apparatus comprises a wearable device.

11. The biometric information detecting apparatus of claim 10, wherein the signal processor is configured to obtain biometric information based on the analyzing of the waveform of the bio-signal, the biometric information comprising at least one from among systolic blood pressure, diastolic blood pressure, oxygen saturation of blood, blood vessel elasticity, speed of blood flow, and arterial stiffness.

12. A method of detecting biometric information in a biometric information detecting apparatus, the method comprising:
    measuring a bio-signal by detecting an optical signal that is modulated by a target object;
    obtaining a low-frequency signal from the bio-signal; and
    in response to determining that the low-frequency signal obtained from the bio-signal is within a reference range, obtaining biometric information by analyzing a waveform of the bio-signal,
    wherein the analyzing the waveform of the bio-signal is not started until it is determined that the low-frequency signal obtained from the bio-signal is within the reference range.

13. The method of claim 12, further comprising:
    in response to determining that the low-frequency signal is not within the reference range, again measuring the bio-signal after a state in which the biometric information detecting apparatus is worn on the target object is adjusted.

14. The method of claim 13, further comprising:
    displaying an indication indicating whether a contact pressure between the biometric information detecting apparatus and a skin of the target object has an acceptable level.

15. The method of claim 14, wherein the displaying comprises displaying an indication that the contact pressure has the acceptable level when the low-frequency signal is within the reference range.

16. The method of claim 12, wherein the bio-signal comprises a PPG signal.

17. The method of claim 12, further comprising:
filtering, by using a band pass filter, the bio-signal so that only the bio-signal of a particular band is passed,
wherein the biometric information is obtained by analyzing a waveform of the filtered bio-signal.

18. The method of claim 12, wherein the low-frequency signal is obtained by passing only the bio-signal of a low frequency band by using a low-frequency band pass filter.

19. The method of claim 18, wherein the low-frequency band pass filter is configured to pass only the bio-signal of a frequency band from DC to about 10 Hz.

20. A biometric information detecting apparatus comprising:

a biometric sensor configured to sense a biometric signal of a user measured through contact with a skin of the user;

a filter configured to filter a low-frequency signal from the biometric signal sensed by the biometric sensor; and a signal processor configured to determine that the biometric signal sensed by the biometric sensor is reliably sensed by the biometric sensor based on the low-frequency signal filtered by the filter, and analyze a waveform of the biometric signal in response to determining that the biometric signal is reliably sensed by the biometric sensor, wherein the signal processor does not start analyzing the waveform of the biometric signal until it is determined that the low-frequency signal filtered by the filter is within a reference range.

\* \* \* \* \*